(12) United States Patent
Rybak et al.

(10) Patent No.: US 7,482,014 B2
(45) Date of Patent: *Jan. 27, 2009

(54) MELANOMA THERAPY

(75) Inventors: Mary Ellen Rybak, Warren, NJ (US); Esther Helen Rose, Westfield, NJ (US)

(73) Assignee: Schering Corporation, Kenilworth, NJ (US)

( * ) Notice: Subject to any disclaimer, the term of this patent is extended or adjusted under 35 U.S.C. 154(b) by 315 days.

This patent is subject to a terminal disclaimer.

(21) Appl. No.: 11/166,862

(22) Filed: Jun. 24, 2005

(65) Prior Publication Data

US 2005/0238621 A1  Oct. 27, 2005

Related U.S. Application Data

(60) Division of application No. 09/904,263, filed on Jul. 12, 2001, now Pat. No. 6,923,966, which is a continuation of application No. 09/545,312, filed on Apr. 7, 2000, now abandoned.

(60) Provisional application No. 60/128,308, filed on Apr. 8, 1999.

(51) Int. Cl.
*A61K 38/21* (2006.01)
*C07K 14/56* (2006.01)

(52) U.S. Cl. .................. 424/195.11; 424/193.1; 424/198.1; 424/85.1; 424/85.2; 424/85.4; 424/85.7; 514/2; 530/402; 530/399

(58) Field of Classification Search ........... 424/85.1, 424/85.2, 85.4, 193.1, 195.11, 198.1, 85.7; 514/2; 530/402, 399
See application file for complete search history.

(56) References Cited

U.S. PATENT DOCUMENTS

| | | | |
|---|---|---|---|
| 4,530,901 A | 7/1985 | Weissmann |
| 4,695,623 A | 9/1987 | Stabinsky |
| 4,766,106 A | 8/1988 | Katre et al. |
| 4,897,471 A | 1/1990 | Stabinsky |
| 4,917,888 A | 4/1990 | Katre et al. |
| 5,382,427 A | 1/1995 | Plunkett et al. |
| 5,711,944 A | 1/1998 | Gilbert et al. |
| 5,762,923 A | 6/1998 | Gross et al. |
| 5,766,582 A | 6/1998 | Yuen et al. |
| 5,766,897 A | 6/1998 | Braxton |
| 5,776,897 A | 7/1998 | Lewis et al. |
| 5,908,621 A | 6/1999 | Glue et al. |
| 5,951,974 A | 9/1999 | Gilbert et al. |
| 5,985,263 A | 11/1999 | Lee et al. |
| 6,362,162 B1 | 3/2002 | Rybak et al. |
| 6,605,273 B2 | 8/2003 | Ryback et al. |
| 6,923,966 B2 | 8/2005 | Rybak et al. |

FOREIGN PATENT DOCUMENTS

| EP | 0 510 356 A1 | 10/1992 |
|---|---|---|
| EP | 0 593 868 A1 | 4/1994 |
| EP | 0 236 987 B1 | 12/1994 |
| EP | 0 809 996 A2 | 12/1997 |
| HU | 196560 B | 12/1998 |
| WO | WO 95/13090 | 5/1995 |
| WO | WO 98/48840 | 5/1998 |
| WO | WO 99/48535 | 9/1999 |

OTHER PUBLICATIONS

Bannink, M. et al., Progress in Neuro-Psychopharmacology & Biological Psychiatry, 29: 109-114, 2005.*

Kefford, R.F., annals of Oncology 14: 358-365, 2003.*

Atzpodien et al., "Home therapy with recombinant interleukin-2 and interferon-α2b in advanced human malignancies," *The Lancet*, 335:1509-1512 (1990).

Atzpodien et al., "Multiinstitutional Home-Therapy Trial of Recombinant Human Interleukin-2 and Interferon Alfa-2 in Progessive Metastatic Renal Cell Carcinoma," *Journal of Clinical Oncology*, 13(2):497-501 (Feb. 1995).

Atzpodien J. et al., "Interleukin-2 in Combination with Interferon-α and 5-Fluorouracil for Metastatic Renal Cell Cancer", *European Journal of Cancer*, 29A(Suppl. 5):S6-S8 (1993).

Bergmann et al., "Daily Alternating Administration of High-Dose Alpha-2b-Interferon and Interleukin-2 Bolus Infusion in Metastatic Renal Cell Cancer," *Cancer* 72(5):1735-1742 (Sep. 1, 1993).

Bruno, René, et al., "Population Pharmacokinetics/Pharmacodynamics of Docetaxel in Phase II Studies in Patients with Cancer", *Journal of Clinical Oncology*, 16(1):187-96 (1998).

Bukowski et al., "Pegylated Interferon Alfa-2b Treatment for Patients with Solid Tumors: A Phase I/II Study", *J. Clin. Oncol.* 20(18):3841-3849 (2002).

Bukowski, "Phase 1 Study of Polyethylene Glycol (PEG) Interferon Alpha-2B (PEG INTRON) in Patients with Solid Tumors", *Proc. Annu. Meet. American Society of Clinical Oncology*, 18:A1719, XP000953163 Abstract (1999).

(Continued)

*Primary Examiner*—Alana M. Harris
*Assistant Examiner*—Anne L Holleran
(74) *Attorney, Agent, or Firm*—Melodie W. Henderson

(57) ABSTRACT

Methods for treating treatment-naive as well as treatment-experienced patients having melanoma to increase the progression-free survival time involving administering a therapeutically effective amount of pegylated interferon-alpha, e.g., preferably pegylated interferon alpha-2b, as adjuvant therapy to definitive surgery are disclosed.

17 Claims, No Drawings

OTHER PUBLICATIONS

Calvert, A.H., et al., "Carboplatin Dosage: Prospective Evaluation of a Simple Formula Based on Renal Function," *Journal of Clinical Oncology*, 7(11):1748-56 (1989).

Cascinelli, N. et al., "Results of Adjuvant Interferon study in WHO Melanoma Programme," *The Lancet*, 343:913-914 (Apr. 9, 1994).

Creagon et al., "Randomized, Surgical Adjuvant Clinical Trial of Recombinant Interferon Alfa-2a in Selected Patients With Malignant Melanoma," *Journal of Clinical Oncology*, 13(13):2776-2783 (Nov. 1995).

Deprés-Brummer et al., "A Phase II Study of Ambulatory Chronomodulated High Dose Interferon (IFNα2a) Against Metastatic Renal Cancer (MRC)," *American Society of Clinical Oncology*, 15:248, Abstract No. 628, (Mar. 1996).

Dutcher et al., "Outpatient Subcutaneous Interleukin-2 and Interferon-Alpha for Metastatic Renal Cell Cancer: Five-Year Follow-up of the Cytokine Working Group Study," *The Cancer Journal from Scientific American*, 3:3 (May/Jun. 1997).

Eisenhauer et al., "The Taxoids, Comparative Clinical Pharmacology and Therapeutic Potential," *Drugs*, 55(1):5-30 (1998).

Eksborg et al., "Plasma pharmacokinetics of idarubicin and its 13-dihydro metabolite-a comparison of bolus versus 2 h infusion during a 3 day course," *Anti-Cancer Drugs*, 8:42-7 (1997).

Escudier et al., "The FNCLCC Crecy Trial: Interleukin 2 (IL2) + Interferon (IFN) is the Optimal Treatment to Induce Response in Metastatic Renal Cell Carcinoma (MRCC)," *American Society of Clinical Oncology*, 15:248, Abstract No. 629, (Mar. 1996).

Fleming et al., "One-Sample Multiplel Testing Procedure for Phase II Clinical Trials," *Biometrics*, 38:143-151 (Mar. 1982).

Forastiere et al., "Pharmacokinetic and Toxicity Evaluation of Five-Day Continuous Infusion versus Intermittent Bolus *cis*-Diamminedichloroplatinum(II) in Head and Neck Cancer Patients," *Cancer Research*, 48:3869-3874 (1988).

Gandhi et al., "Compound GW506U78 in Refractory Hematologic Malignancies: Relationship Between Cellular Pharmacokinetics and Clinical Response," *Journal of Clinical Oncology*, 16(11):3607-15 (1998).

Gebrosky et al., "Treatment of Renal Cell Carcinoma with 5-Fluorouracil and Alfa-Interferon", *Urology*, 50(6):863-868 (1997).

Gennaro, A., "Antineoplastic and Immunoactive Drugs," Remington's 18th Ed., (1990).

Gitlitz et al., "Fluoropyrimidines Plus Interleukin-2 and Interferon-α in the Treatment of Metastatic Renal Cell Carcinoma: The UCLA Kidney Cancer Program," *American Society of Clinical Oncology*, 15:248, Abstract No. 630, (Mar. 1996).

Goldman, "Optimizing Treatment for Chronic Myeloid Leukemia," *The New England Journal of Medicine*, 337(4):270-271 (Jul. 24, 1997).

Guilhot et al., "Interferon Alfa-2b Combined with Cytarabine Versus Interferon Alone in Chronic Myelogenous Leukemia," *The New England Journal of Medicine*, 337(4):223-229 (Jul. 24, 1997).

Hasford et al., "Interferon-α and Hydroxyurea in Early Chronic Myeloid Leukemia: A Comparative Analysis of the Italian and German Chronic Myeloid Leukemia Trials With Interferon-α," *Blood*, 87(12):5384-5391 (1996).

Hehlman et al., "Randomized Comparison of Interferon-α With Busulfan and Hydroxyurea in Chronic Myelogenous Leukemia," *Blood*, 84(12):4064-4077 (Dec. 15, 1994).

Kantarjian et al., "Chronic Myelogenous Leukemia: A Concise Update," *Blood*, 82(3):691-703 (Aug. 1, 1993).

Kantarjian et al., "Prolonged Survical in Chronic Myelogenouos Leukemia after Cytogenetic Response to Interferon-α Therapy," *Ann Intern Med.*, 122:254-261 (1995).

Kantarjian et al., "Treatment of Chronic Myelogenous Leukemia: Current Status and Investigational Options," *Blood*, 87(8):3069-3081 (Apr. 15, 1996).

Kirkwood et al., "Interferon Alfa-2b Adjuvant Therapy of High-Risk Resected Cutanenous Melanoma: The Eastern Cooperative Oncology Group Trial EST 1684," *Journal of Clinical Oncology*, 14(1):7-17 (Jan. 1996).

Legha, Sewa S., "The Role of Interferon Alfa in the Treatment of Metastatic Melanoma," *Seminars in Oncology*, 24(1 Suppl 4): S4-24-54-31 (Feb. 1997).

Levens et al., "Long-Term Interferon Treatment in Metastatic Renal Cell Carcinoma," *Eur Urol.*, 16:378-381 (1989).

Négrier et al., "Intensive Regimen of Cytokines with Interleukin-2 and Interferon Alfa-2B in Selected Patients with Metastatic Renal Carcinoma," *Journal of Immunotherapy*, 17:62-68 (1995).

Nicolaou et al., "Total Synthesis of Taxol. 1. Retrosynthesis, Degradation, and Reconstitution," *J. Am. Chem. Soc.*, 117:624-633 (1995).

Ohnishi et al., "A Randomized Trial Comparing Interferon-α With Busulfan for Newly Diagnosed Chronic Myelogenous Leukemia in Chronic Phase," *Blood*, 86(3):906-916 (Aug. 1, 1995).

Osoba et al., "Modification of the EORTC QLQ-C30 (version 2.0) based on content validity and reliability testing in large samples of patients with cancer," *Quality of Life Research*, 6:103-108 (1997).

Ozer et al., "Prolonged Subcutaneous Administration of Recombinant α2b Interferon in Patients wtih Previously Untreated Philadelphia Chromosome-Positive Chronic-Phase Chronic Myelogenous Leukemia: Effect of Remission Duration and Survival: Cancer and Leukemia Group B Study 8583," *Blood*, 82(10):2975-2984 (Nov. 15, 1993).

Rodman et al., "Clinical Pharmacodynamics of Continuous Infusion Teniposide: Systemic Exposure as a Determinant of Response in a Phase I Trial," *Journal of Clinical Oncology*, 5(7):1007-1014 (1987).

Rosenberg et al., "Experience with the Use of High-Dose Interleukin-2 in the Treatment of 652 Cancer Patients," *Ann. Surg.*, 210(4):474-485 (1989).

Sagaster et al., "Randomised Study Using IFN-α versus IFN-α plus coumarin and cimetidine for treatment of advanced renal cel cancer," *Annals of Oncology*, 6:999-1003 (1995).

Shalinsky et al., "Antitumor efficacy of AG3340 associated with maintenance of minimum effective plasma concentrations and not total daily dose, exposure or peak plasma concentrations," *Investigational New Drugs*, 16:303-13 (1999).

Sokal et al., "Preferential Inhibition by Cytarabine of CFU-GM From Patients With Chronic Granulocytic Leukemia," *Cancer*, 59:197-202 (Jan. 1, 1987).

Takitani, Kimitaka, et al., "4-Oxo Retinoic Acid for Refractory Acute Promyelocytic Leukemia in Children with All-*Trans* Retinoic Acid Therapy," *J. Nutr. Sci. Vitaminol.*, 41:493-98 (1995).

Talpaz et al., "Phase I Study Of Pegylated-Interferon α-2A (PEGASYS™) In Patients With Chronic Myelogenous Leukemia (CML)", *Blood*, 94(10, Suppl. 1, part 1):530A, (Nov. 15, 1999).

Talpaz et al., "Phase I Study Of Polyethylene Glycol (PEG) Interferon Alpha-2B (Intron-A) in CML Patients", *Blood*, 92(10, Suppl. 1 part 1-2):251A, (Nov. 15, 1998).

Talpaz et al., "Interferon-Alpha Produces Sustained Cytogenetic Responses in Chronic Myelogenouos Leukemia," *Annals of Internal Medicine*, 114:7 (Apr. 1, 1991).

The Italian Cooperative Study Group on Chronic Myeloid Leukemia, "Interferon Alfa-2a as Compared with Conventional Chemotherapy for the Treatment of Chronic Myeloid Leukemia," *The New England Journal of Medicine*, 330(12):820-825 (Mar. 24, 1994).

Umeda et al., "Phase II Study of Alpha Interferon on Renal Cell Carcinoma," *Cancer*, 58:1231-1235 (Sep. 15, 1986).

Walther et al., "Treatment of Metastatic Renal Cell Carcinoma (RCC) with Continuous Infusion 5-Fluorouracil and Interferon Alpha-2A in the Home Setting: A Phase I-II Trial", *Proceedings of the American Urological Association*, 155:388A (May 1996 Supplement).

\* cited by examiner

MELANOMA THERAPY

This application is a divisional of application Ser. No. 09/904,263, filed Jul. 12, 2001, now U.S. Pat. No. 6,923,966, which is a continuation of Ser. No. 09/545,312, filed Apr. 7, 2000, abandoned, which claims the benefit of U.S. provisional patent application Ser. No. 60/128,308, filed Apr. 8, 1999.

Throughout this disclosure, various publications, patents and patent applications are referenced. The disclosures of these publications, patents and patent applications are herein incorporated by reference.

BACKGROUND OF THE INVENTION

This invention relates to an improved therapy for treating patients having melanoma after definitive surgical removal of the lesions by administering a therapeutically effective dose of pegylated interferon-alpha for a time sufficient to increase progression-free survival time.

Melanoma incidence is increasing at a rate that exceeds all that for other solid tumors. Patients with primary melanoma of greater than 4 mm or metastatic melanoma involving regional lymph nodes possess a 50 to 90% mortality risk following surgical excision of the primary melanomas.

Recently, the Eastern Cooperative Oncology Group ("ECOG") published results of the use of interferon alpha-2b in patients with stage III cutaneous melanoma as adjuvant therapy following surgery for deep primary (T4) or regionally metastatic (N1) melanoma (Kirkwood, J. M., et al. *J. Clin. Oncol.*, Vol 14: (1996) pages 4-17.) The interferon alpha-2b therapy used by ECOG involved an induction phase of 20 million IU of interferon alpha-2b per square meter of body surface area ($m^2$) administered intravenously ("IV") daily for five days every week for four weeks followed by maintenance interferon alpha therapy of 10 million IU/$M^2$ administered subcutaneously ("SC") three times a week ("TIW") for 48 weeks. A significant improvement in median disease-free survival and overall survival were observed versus control (observation) despite dosage reductions or delays for toxicity in 50% of the patients during the IV induction therapy phase and in 48% of the patients in the SC maintenance phase. Hematologic, neurologic and constitutional toxicities occurred among these patients requiring dose reduction or withdrawal from the interferon alpha therapy. Subject compliance with the dosage and dosage regimen during both phases is considered to be important to achieve maximum clinical benefit. Accordingly, there is a need for improved therapy for treating patients having melanoma with higher patient compliance.

SUMMARY OF THE INVENTION

The present invention provides a method of treating a patient having melanoma which has been surgically removed, which comprises administering to such a patient a therapeutically effective dose of pegylated interferon alpha for a time period sufficient to increase the progression-free survival time.

The present invention also provides a method of treating a patient having cutaneous melanoma which has been surgically removed, which comprises administering to said patient an effective amount of pegylated interferon-alpha once a week for a time period sufficient to increase progression-free survival time.

The present invention further provides a method of treating a patient having cutaneous melanoma which has been surgically removed which comprises administering to such a patient about 3.0 micrograms/kg to about 9.0 micrograms/kg of pegylated interferon alpha-2b once a week for a time period sufficient to increase progression-free survival time. In preferred embodiments, 6.0 micrograms per kilogram is dosed weekly to a patient for eight weeks, and 3.0 micrograms per kilogram or less weekly is dosed to the patient for a period of five years minus the eight weeks of initial dosage. If less than 3.0 micrograms per kilogram are dosed to the patient, preferably the dose reduction steps are 3.0-2.0-1.0 micrograms per kilogram.

The present invention further provides a method comprising the step of marketing a therapeutically effective dose of interferon alpha for administration to a patient with melanoma within about 60 days of surgery in a protocol extending for a time period of at least about 100 weeks.

DETAILED DESCRIPTION OF THE INVENTION

The present invention provides an improved method of treating patients with melanoma especially those in State IIB (lesions>4 mm, but without positive nodes)and Stage III (lesions>4 mm and node-positive) primary cutaneous melanoma, preferably after surgery for their State IIB or Stage III melanoma. The improved method provides a safer and more efficacious and tolerable adjuvant therapy treatment for melanoma by use of weekly injections of pegylated interferon. The melanoma patients treatable in accordance with the improved method of the present invention include those newly diagnosed with this disease who were free of disease 56 days post surgery but at high risk for systemic recurrence of the disease. The term "high risk patients" as used herein means those melanoma patients with lesions of Breslow thickness >4 mm as well as those patients with lesions of any Breslow thickness with primary or recurrent nodal involvement. Melanoma patients intolerant or resistant to interferon alpha therapy are also included. Treatment with pegylated interferon alpha in accordance with the present invention will continue for a minimum of about two years (about 100-104 weeks) and up to five years, unless there is clinical evidence of disease progression, unacceptable toxicity or the patient requests that the therapy be discontinued.

When the pegylated interferon-alpha administered is a pegylated interferon alpha-2b, the therapeutically effective amount of pegylated interferon alpha-2b administered is in the range of about 3.0 to about 9.0 micrograms per kilogram of pegylated interferon alpha-2b administered once a week (QW), preferably in the range of about 4.5 to about 6.5 micrograms per kilogram of pegylated interferon alpha-2b QW, more preferably in the range of about 5.5 to about 6.5 micrograms per kilogram of pegylated interferon alpha-2b QW, and most preferably in the range of about 6.0 micrograms per kilogram of pegylated interferon alpha-2b administered QW.

In preferred embodiments, 6.0 micrograms per kilogram is dosed weekly to a patient for eight weeks, and 3.0 micrograms per kilogram or less weekly is dosed to the patient for a period of five years minus the eight weeks of initial dosage. If less than 3.0 micrograms per kilogram are dosed to the patient, preferably the dose reduction steps are 3.0-2.0-1.0 micrograms per kilogram.

When the pegylated interferon-alpha administered is a pegylated interferon alpha-2a, the therapeutically effective amount of pegylated interferon alpha-2a administered is in the range of about 50 micrograms to about 500 micrograms once a week("QW"), preferably about 200 micrograms to about 250 micrograms QW.

The term "pegylated interferon alpha" as used herein means polyethylene glycol modified conjugates of interferon alpha, preferably interferon alpha-2a and -2b. The preferred polyethylene-glycol-interferon alpha-2b conjugate is $PEG_{12000}$-interferon alpha 2b. The phrases "12,000 molecular weight polyethylene glycol conjugated interferon alpha" and "$PEG_{12000}$-IFN alpha" as used herein mean conjugates such as are prepared according to the methods of International Application No. WO 95/13090 and containing urethane linkages between the interferon alpha-2a or -2b amino groups and polyethylene glycol having an average molecular weight of 12000.

The preferred $PEG_{12000}$-interferon alpha-2b is prepared by attaching a PEG polymer to the epsilon amino group of a lysine residue in the IFN alpha-2b molecule. A single $PEG_{12000}$ molecule is conjugated to free amino groups on an IFN alpha-2b molecule via a urethane linkage. This conjugate is characterized by the molecular weight of $PEG_{12000}$ attached. The $PEG_{12000}$-IFN alpha-2b conjugate is formulated as a lyophilized powder for injection. The objective of conjugation of IFN alpha with PEG is to improve the delivery of the protein by significantly prolonging its plasma half-life, and thereby provide protracted activity of IFN alpha.

The term "interferon-alpha" as used herein means the family of highly homologous species-specific proteins that inhibit viral replication and cellular proliferation and modulate immune response. Typical suitable interferon-alphas include, but are not limited to, recombinant interferon alpha-2b such as Intron-A interferon available from Schering Corporation, Kenilworth, N.J., recombinant interferon alpha-2a such as Roferon interferon available from Hoffmann-La Roche, Nutley, N.J., recombinant interferon alpha-2C such as Berofor alpha 2 interferon available from Boehringer Ingelheim Pharmaceutical, Inc., Ridgefield, Conn., interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alpha-n3 a mixture of natural alpha interferons made by Interferon Sciences and available from the Purdue Frederick Co., Norwalk, Conn., under the Alferon Tradename. The use of interferon alpha-2a or alpha-2b is preferred. Since interferon alpha-2b, among all interferons, has the broadest approval throughout the world for treating chronic hepatitis C infection, it is most preferred. The manufacture of interferon alpha-2b is described in U.S. Pat. No. 4,530,901.

Other interferon alpha conjugates can be prepared by coupling an interferon alpha to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alpha-polymer conjugates are described in U.S. Pat. No. 4,766,106, U.S. Pat. No. 4,917,888, European Patent Application No. 0 236 987, European Patent Application Nos. 0 510 356, 0 593 868 and 0 809 996 (pegylated interferon alpha-2a) and International Publication No. WO 95/13090.

Pharmaceutical composition of pegylated interferon alpha-suitable for parenteral administration may be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g. human serum albumin), toxicity agents (e.g. NaCl), preservatives (e.g. thimerosol, cresol or benylalcohol), and surfactants (e.g. tween or polysorabates) in sterile water for injection. The pegylated interferon alpha-may be stored as lyophilized powders under a refrigeration at 2°-8° C. The reconstituted aqueous solutions are stable when stored between 2° and 8° C. and used within 24 hours of reconstitution. See for example U.S. Pat. Nos. 4,492,537; 5,762,923 and 5,766,582. The reconstituted aqueous solutions may also be stored in prefilled, multi-dose syringes such as those useful for delivery of drugs such as insulin. Typical suitable syringes include systems comprising a prefilled vial attached to a pen-type syringe such as the NOVOLET Novo Pen available from Novo Nordisk, as well as prefilled, pen-type syringes which allow easy self-injection by the user. Other syringe systems include a pen-type syringe comprising a glass cartridge containing a diluent and lyophilized pegylated interferon alpha powder in a separate compartment.

The term "patients having melanoma" as used herein means any patient having melanoma and includes treatment-naive patients as well as treatment-experienced patients as well as patients in the Stage IIB or Stage III cutaneous melanoma. All patients having melanoma are preferably treated by wide excision of the primary melanoma lesion prior to initiation of the improved therapy of the present invention.

The term "treatment-naive patients" as used herein means patients with melanoma including newly-diagnosed melanoma patients who have never been treated with any chemotherapeutic drugs, e.g. dacarbazine ("DTIC") or immunotherapy, e.g., IL-2 as well as any interferon, including but not limited to interferon alpha, or pegylated interferon alpha. All treatment-naive patients having melanoma are preferably treated by wide excision of the primary melanoma lesion prior to initiation of the improved therapy of the present invention.

The term "treatment-experienced patients" as used herein means those patients who have initiated some form of chemotherapeutic drug, e.g., DTIC or immunotherapy including, but not limited to interferon-alpha, IL-2 and GMCSF. All treatment-experienced patients having melanoma are preferably treated by wide excision of the primary melanoma lesion prior to initiation of the improved therapy of the present invention.

The term "primary cutaneous melanoma" as used herein means histologically proven primary cutaneous melanoma as defined by the current (1992) American Joint Committee on Cancer Staging Criteria ("AJCC"): in the AJCC Manual for Strategy of Cancer (4th edition) Philadelphia, Pa. Lippincott Publishers 1992 and includes (a) node negative stage IIB disease with deep primary melanomas of Breslow depth more than 4 mm and (b)node positive stage III disease defined, as follows: (1) deep primary melanomas of Breslow depth more than 4 mm (designated CS1 PS1: T4N0M0); (2) primary melanomas of any tumor stage in the presence of N1 regional lymph node metastasis detected at elective lymph node dissection with clinically inapparent regional lymph node metastasis (designated CS1 PS2: any TpN1 M0); (3) clinically apparent N1 regional lymph node involvement synchronous with primary melanoma of T1-4 (designated CS2 PS2: any TcN1M0); and (4) regional lymph node recurrence at any interval after appropriate surgery for primary melanoma of any depth (designated CS2R: TxrN1 M0 recurrent). Patients in groups 1 to 3 were required to enter this study within 56 days of first primary melanoma biopsy. Patients with regional nodal relapse in group 4 were required to enter this study within 42 days of lymphadenectomy.

All patients with stage III melanoma should be treated by wide excision of the primary melanoma lesion.

Patients with clinically positive nodes in the groin, axilla or neck should have a full lymphadenectomy to surgically remove these cites.

All surgery should be completed within 56 days prior to randomization into this clinical study.

The term "progression-free survival time" ("PFST") as used herein means the time from initiation of melanoma treatment in accordance with the present invention to the documentation of disease progression or recurrence by histological or cytological evidence The progression-free survival time expected for melanoma patients treated in accordance with the method of this invention is at least about 4 years from initiation of the melanoma therapy of this invention; preferably the PFST is in the range of about 30 to about 43 months from initiation of the melanoma therapy of this invention.

The increase in the progression-free survival time expected for melanoma patients treated in accordance with the method of this invention is greater than about 1.0 years to about 1.5 years compared to control (observation).

The following criteria of treatment failure constitute the only acceptable evidence of disease recurrence or progression:

Lung/Liver:
Positive cytology or biopsy in the presence of a single new lesion or the appearance of multiple lesions consistent with metastatic disease.

Central Nervous System:
A positive brain CT or MRI scan or Cerebrospinal fluid (CSF) cytology.

Cutaneous, Subcutaneous and Lymph Node Recurrence:
Positive cytology or biopsy.

Bone and Other Organs:
Positive cytology or biopsy in the presence of a single new lesion or the appearance of multiple lesions consistent with metastatic disease identified by two different radiologic studies: i.e., positive gallium scan and contrast GI series or ultrasound, x-ray or CT of abdomen for abdominal disease.

The term "prohibited medications" as used herein includes the following:
  a) Other chemotherapy, hormonal, immunologic, biologic or radiation therapy.
  b) Colony stimulating factors including erythropoietin and G-CSF.
  c) Other investigational drugs.
  d) Chronic systemic corticosteroid therapy.

Melanoma patients treated in accordance with the method of the present invention should not receive any of the above-listed prohibited medications during the treatment period.

Pegylated interferon-alpha formulations are not effective when administered orally, so the preferred method of administering the pegylated interferon-alpha is parenterally, preferably by subcutaneous, IV, or IM, injection. Of course, other types of administration of both medicaments, as they become available are contemplated, such as by nasal spray, transdermally, by suppository, by sustained release dosage form, and by pulmonary inhalation. Any form of administration will work so long as the proper dosages are delivered without destroying the active ingredient.

The following Clinical Study Design may be used to treat melanoma patients in accordance with the method of the present invention. Many modifications of this Clinical Study Design protocol will be obvious to the skilled clinician, and the following Study Design should not be interpreted as limiting the scope of the method of this invention which is defined by the claims listed hereinafter.

Clinical Study Design

This is a Phase II/III randomized, controlled, multicenter, open-label study designed to assess he safety, efficacy, and impact on quality of life of PEG Intron (pegylated interferon alpha 2b i.e. $PEG_{12000}$-interferon alpha 2b and INTRON® A (interferon alpha 2b), which are each available from Schering Corporation, Kenilworth, N.J., and the population pharmacokinetics of PEG Intron when given as adjuvant therapy in subjects with resected Stage III node-positive cutaneous melanoma. It is anticipated that approximately 450 subjects will be enrolled, with 225 subjects randomized to each treatment group.

Subjects will enter the study within 56 days of definitive surgery for their Stage III melanoma and will be randomized to one of the two treatment groups shown below. Definitive surgery includes wide surgical excision of the primary melanoma and lymphadenectomy of all clinically positive nodes in the groin, axilla and neck. All surgery should be complete at least 56 days prior to randomization.

Group A: INTRON® A
20 MIU/m$^2$/day IV 5 days/week×4 weeks, followed by 10 MIU/m$^2$ SC TIW×48 weeks.

Induction Therapy: 20 MIU/m$^2$/day IV 5 days a week for 4 weeks

All subjects randomized to Treatment Group A, will begin induction therapy with intravenous INTRON® A, 20 million international units/m$^2$/day, 5 days/week for 4 weeks. Acetaminophen (500-1000 mg) may be given in the clinic 30 minutes prior to receiving the first dose of INTRON® A. Subjects should be observed for 2 hours after the first dose. Acetaminophen (500-650 mg PO q 4-6 hours) should be continued as needed, and should not exceed 3000 mg/day.

Maintenance Therapy: 10 MIU/m$^2$ SC TIW for 48 weeks.

After induction therapy, subjects will continue on maintenance therapy and receive INTRON® A, 10 million international units/m$^2$/day, SC three times weekly for 48 weeks.

Group B: PEG Intron: $PEG_{12000}$-interferon alpha-2b, 6.0 µg/kg, SC once weekly for 2 years.

Subjects randomized to treatment Group B will receive $PEG_{12000}$-interferon alpha-2b, 6.0 µg/kg, SC once weekly for 2 years. Acetaminophen (500-1000 mg) may be given in the clinic 30 minutes prior to receiving the first dose of PEG Intron. Subjects should be observed for 2 hours after the first dose. Acetaminophen (500-650 mg PO q 4-6 hours) should be continued as needed, and should not exceed 3000 mg/day.

Duration of Study and Visit Schedule

Treatment with either $PEG_{12000}$-interferon alpha 2b (about 104 weeks) or INTRON® A (52 weeks) will continue as scheduled unless there is evidenced of disease recurrence, unacceptable toxicity, or the subject requests that therapy be discontinued. Tolerability of the respective study treatment and quality of life will be assessed from clinical observation, routine lab oratory testing, and quality of life assessments over the course of therapy. Following completion of therapy, subjects will continue to be followed for evidenced of disease recurrence and will complete quality of life assessments. If the melanoma recurs, further treatment will be at the discretion of the physician. All subjects will be followed for survival, regardless of when they discontinue therapy. Analyses of relapse-free and overall survival, regardless of when they discontinue therapy. Analyses of relapse-free and overall survival will be event driven.

The duration of this study is based upon achieving a therapeutic response, and will be determined for each subject individually.

The study population will include male and female patients with cutaneous melanoma and will be included if they meet the following inclusion and exclusion criteria:

Subject Inclusion Criteria

A subject is eligible to participate in this study if he or she:
a) Subjects must have histologically documented primary cutaneous melanoma meeting one of the following staging Criteria:
   Primary melanoma of any stage in the presence of N1 regional lymph node metastases detected at elective lymph node dissection or sentinel node biopsy, with clinically inapparent regional lymph node metastasis (any $pTN_1M_0$).
   Clinically apparent N1 or N2a regional lymph node involvement synchronous with primary melanoma of $T_{1-4}$ (any $pTrN_{1-2a}M_0$).
   Regional lymph node recurrence at any interval after appropriate surgery for primary melanoma of any depth (any $pTrN_{1-2a}M_0$).
b) Subjects must have had all known disease completely resected with adequate surgical margins within 56 days prior to randomization into the study.
c) Subjects must have an ECOG performance status of 0 or 1 as defined by Minna, J D, et al. "Cancer of the Lung" in DeVita V, et al. eds., Cancer: Principles and Practiced of Oncology, Lippincott, Philadelphia, Pa. 1989 at page 536.
d) Subjects must be between 18-70 years old.
e) Subjects must have adequate hepatic, renal and bone marrow function as defined by the following parameters obtained within 14 days prior to initiation of study treatment.
   1) Hematology:
      White Blood count (WBC) $\geq 3,000$ cells/μL.
      Hemoglobin concentration $\geq 9$ g/dL.
   2) Renal and hepatic function:
      Serum creatinine $\leq 2.0$ mg/dL or calculated creatinine clearance of $\geq 50$ mL/minute.
      Serum bilirubin <2 times the upper limit of normal (ULN), unless due to infiltration by disease.
      AST/ALT (SGOT/SGPT) <2 times ULN.
f) has submitted a written voluntary informed consent before study entry, is willing to participate in this study and will complete all follow up assessments.

Subject Exclusion Criteria

A subject is not eligible to participate in this study if he or she:
a) Subjects who have received any prior chemotherapy, immunotherapy hormonal or radiation therapy for melanoma.
b) Subjects who have evidence of distant or non-regional lymph node metastases, in-transit metastases, or positive lymph nodes with an unknown primary.
c) Subjects whose disease cannot be completely surgically resected because of gross extracapsular extension.
d) Subjects who have previously received interferon-α for any reason. (Such patients however, are still considered treatable in accordance with the method of this invention but are only excluded from this registration study.)
e) Subjects who have severe cardiovascular disease, i.e., arrhythmias requiring chronic treatment, congestive heart failure (NYHA Class III or IV) or symptomatic ischemic heart disease as defined by Bruce RA: Evaluation of Functional Capacity and Exercise Tolerance of Cardiac Subjects" in Mod. Concepts Cardiovasc Dis 1956; 25-321.
f) Subjects who have a history of neuropsychiatric disorder requiring hospitalization.
g) Subjects with thyroid dysfunction not responsive to therapy.
h) Subjects with uncontrolled diabetes mellitus.
I) Subjects with a history of prior malignancy within the past 5 years other than surgically cured non-melanoma skin cancer or cervical carcinoma in situ.
j) Subjects who have a history of seropositivity for HIV.
k) Subjects who are pregnant, lactating, or of reproductive potential and not practicing an effective means of contraception.
l) Subjects with active and/or uncontrolled infection, including active hepatitis.
m) Subjects with a medical condition requiring chronic systemic corticosteroids.
n) Subjects who are known to be actively abusing alcohol or drugs.
o) Subjects who have received any experimental therapy within 30 days prior to randomization in this study.
p) Subjects who have not recovered from the effects of recent surgery.

Subject Discontinuation Criteria

It is the right and duty of the clinical investigator to interrupt the treatment of any subject whose health or well being may be threatened by continuation in this study.

Subjects may be discontinued prior to completion of this study for any of the following reasons:
a) Develops documented progression or recurrence of disease, as defined herein above.
b) Has a clinically significant adverse event as determined by the Principal Investigator.
c) Requests to be withdrawn from the study.
d) Is unable to complete the study evaluations/visits because of unforeseen circumstances.
e) Develops other conditions for which, in the investigator's opinion warrants withdrawal from the study
f) Develops severe depression or any other psychiatric disorder requiring hospitalization.
g) Experiences a serious allergic response to the study drug manifested by angioedema, bronchoconstriction or anaphylaxis.
h) Receives treatment with a prohibited medication as indicated herein above.
I) Experiences recurrent toxicities despite dose modifications as described herein below.

All subjects will be followed for survival, regardless of when they go off study. Subjects who discontinue for reasons other than recurrence of disease should also be followed for recurrence and survival.

Analysis of Primary and Secondary Endpoints

The primary endpoint will be progression-free survival (PFS) time, defined to be the time from randomization to progression or death. PFS will be assessed by clinical observation, with recurrence documented by appropriate radiographic and histologic methods, and confirmed by Independent Central Review.

The secondary endpoints will be overall survival, safety, quality of life, and population pharmacokinetics (PK). Safety and tolerability will be assessed from clinical observation and routine laboratory testing over the course of therapy. Health-Related Quality of Life (HQL) will be assessed from an HQL questionnaire.

Population pharmacokinetics will be assessed from periodic serum sampling in the PEG Intron group.

Subjects enrolled in Group A who are not able to tolerate the IV induction dose regimen despite dose modification, should stop the IV regimen but should not be discontinued from the study. After resolution of toxicity, they may enter the INTRON® A maintenance phase with the full maintenance dose.

What is claimed is:

1. A method of treating a patient having Stage IIB or Stage III melanoma which has been surgically removed, which comprises administering to the patient a first dose of 6.0 micrograms/kg of $PEG_{12000}$ interferon alpha-2b once a week for eight weeks, and then administering to the patient a second dose of 3.0 or less micrograms/kg of $PEG_{12000}$ interferon alpha-2b once a week for the remainder of a five year treatment period.

2. The method of claim 1, wherein the patient is a treatment-naive patient.

3. The method of claim 1, wherein the patient is a treatment-experienced patient.

4. The method of claim 3, wherein the treatment-experienced patient has been previously treated with immunotherapy.

5. The method of claim 4, wherein the treatment-experienced patient has been previously treated with interferon alpha.

6. The method of claim 3, wherein the treatment-experienced patient has been previously treated with dacarbazine.

7. The method of claim 1, wherein the patient has N1 regional lymph node metastasis detected at elective lymph node dissection with clinically inapparent regional lymph node metastasis.

8. The method of claim 1, wherein the patient has Stage IIB melanoma.

9. The method of claim 1, wherein the patient has Stage III melanoma.

10. The method of claim 1, wherein the patient has clinically apparent N1 regional lymph node involvement synchronous with primary melanoma of T1-4.

11. A method of treating a patient having Stage III melanoma which has been surgically removed, which comprises administering to the patient a first dose of 6.0 micrograms/kg of $PEG_{12000}$ interferon alpha-2b once a week for eight weeks, and then administering to the patient a second dose of $PEG_{12000}$ interferon alpha-2b once a week for the remainder of a total treatment period of five years, wherein the second dose starts at 3.0 micrograms/kg and is then reduced to 2.0 micrograms/kg.

12. The method of claim 11, wherein the second dose is further reduced to 1.0 micrograms/kg.

13. The method of claim 11, wherein the patient is a treatment-naive patient.

14. The method of claim 11, wherein the patient is a treatment-experienced patient.

15. The method of claim 14, wherein the treatment-experienced patient has been previously treated with immunotherapy.

16. The method of claim 14, wherein the treatment-experienced patient has been previously treated with interferon alpha.

17. The method of claim 11, wherein the patient has N1 regional lymph node metastasis detected at elective lymph node dissection with clinically inapparent regional lymph node metastasis.

* * * * *